United States Patent [19]
Luck et al.

[11] Patent Number: 5,257,182
[45] Date of Patent: Oct. 26, 1993

[54] MORPHOLOGICAL CLASSIFICATION SYSTEM AND METHOD

[75] Inventors: Randall L. Luck, Brooklyn; Richard Scott, New York, both of N.Y.

[73] Assignee: Neuromedical Systems, Inc., Suffern, N.Y.

[21] Appl. No.: 647,438

[22] Filed: Jan. 29, 1991

[51] Int. Cl.$^5$ ............................................. G06F 15/00
[52] U.S. Cl. .................................. 364/413.1; 382/36; 395/924
[58] Field of Search ........................ 364/413.1, 413.08; 382/36; 395/924

[56] References Cited

U.S. PATENT DOCUMENTS

| | | | |
|---|---|---|---|
| 4,128,828 | 11/1978 | Resnick et al. | 364/413.08 |
| 4,404,683 | 9/1983 | Kobayashi et al. | 382/6 |
| 4,965,725 | 10/1990 | Rutenberg | 364/413.1 |

OTHER PUBLICATIONS

IEEE Spectrum 1988, Mar. 1988, Hecht-Nielsen, "Neurocomputing: Picking The Human Brain".
JAMA, Feb. 3, 1989, vol. 261, No. 5, pp. 737-743, Koss, "The Papanicolaou Test For Cervical Cancer Detection".
GB 2093586, Feb. 1982, Bacus "Apparatus For Classification of Cells".
Computer Vision, Graphics and Image Processing, 35, pp. 283-305, 1986, Serra, "Introduction To Mathematical Morphology".
Diagnostics & Clinical Testing, Jan. 1990, Eisner, vol. 28, No. 1, p. 10, "Help For The Weary: An Automated Pap Smear Screening System".
IEEE International Conference on Neural Networks, San Diego, vol. 1, Jul. 1988, Egbert et al., pp. 561-568, "Preprocessing of Biomedical Images . . . ".
Aspex Incorporated Brochure, Dec. 1989, Luck "Operation of the NSI AMIP System".
Aspex Incorporated Brochure, Aspex "Supercomputer For Real-Time Image Processing Aspex's Pip".
Computer Vision, Graphics and Image Processing 35, pp. 333-355, 1986 Sternberg, "Grayscale Morphology".
Acta Neurochirurgica, Suppl 41, 1987, pp. 51-67, Fukushima, K. "Self-Organizing Neural Network Models For Visual Pattern".
Applied Optics, vol. 26, No. 23, 1987, Fukushima, K. "Neural Network Model For Selective Attention In Visual".
Aspex Incorporated Brochure, Luck, "An Overview of the Pipe System".

*Primary Examiner*—Roy N. Envall, Jr.
*Assistant Examiner*—Laura Brutman
*Attorney, Agent, or Firm*—Renner, Otto, Boisselle & Sklar

[57] ABSTRACT

A method of classifying cells based upon their morphology includes a method of classifying objects in a cytological specimen, including the steps of obtaining a first image of at least part of a cytological specimen, classifying objects in the first image on the basis of a predetermined criteria, obtaining a second image of at least one of the objects most likely to have a predetermined criteria, and displaying at least part of the second image to produce a visual display of at least one of the objects most likely to have a predetermined criteria. The method of classifying objects in a specimen includes the steps of obtaining a first digital representation of at least part of the cytological specimen, storing the first digital representation, performing a first filtering operation to filter out images in the first representation that are the approximate size of a malignant or premalignant cell or smaller to produce a second digital representation, removing the images in the second representation from the images in the first representation to produce a third representation, performing a second filtering operation to filter out images in the first representation that are the approximate size of premalignant or malignant cell or larger than the approximate size of a premalignant or malignant cell to produce a fourth representation, and eliminating the images in the fourth representation from the images in the third representation to produce a representation having substantially only images the approximate size of a premalignant or malignant cell.

21 Claims, 5 Drawing Sheets

MORPHOLOGICAL CLASSIFICATION SYSTEM AND METHOD

TECHNICAL FIELD OF THE INVENTION

This invention relates generally to classification, particularly to cytology, and, more particularly, to a method and apparatus for quickly and accurately classifying cells based on cellular morphology.

BACKGROUND OF THE INVENTION

In the medical industry there is often the need for an experienced laboratory technician to review a specimen of biological matter for the presence of cells of a certain cellular type. An example of this is the need to review a pap smear slide for the presence of malignant or premalignant cells. A pap smear often contains as many as 100,000 to 200,000 or more cells and other objects, each of which a technician must individually inspect in order to determine the possible presence of very few malignant or premalignant cells. Pap smear tests, as well as other tests requiring equally exhausting cell inspection techniques, have therefore suffered from a high false negative rate due to the tedium and fatigue imposed upon the technician.

Several thousand women die each year in the United States alone from cervical cancer; a cancer from which a woman theoretically has a high probability of survival if detected in its early in situ stages. If not detected early, however, the chances of survival may decrease drastically. If a malignant cell in a pap smear is missed, by the time the woman has another pap smear performed the cancer may have advanced to its invasive stage from which a woman has a much smaller chance of survival. Consequently, the importance of detecting the presence of only one or a few malignant or premalignant cells among the hundreds of thousands of cells in a smear cannot be overstated. Unfortunately, present manual screening methods are inaccurate. In fact, recently some laboratories have been found to have incorrectly classified as benign up to 30% of the specimens containing malignant or premalignant cells. Also unfortunate is that many prior attempts to automate the cell inspection or classification have been unsuccessful.

Predominately, these prior attempts at automation have relied on feature extraction, template matching and other statistical or algorithmic methods alone. These attempts have required expensive and time-consuming cell preparations to distribute the cells and other objects over a slide so that none of the cells or objects overlap. However, even then these attempts have been unsuccessful at accurately classifying specimens in a reasonable time frame.

These difficulties have been overcome by combining an algorithmic or statistical primary classifier with a neural network based secondary classifier as disclosed in U.S. Pat. No. 4,965,725, and U.S. patent application Ser. Nos. 07/420,105, 07/425,665, 07/502,611 and 07/610,423, which are incorporated in their entireties by this reference. A commercially available automated pap smear screener, using a primary classifier in conjunction with a neurocomputer based secondary classifier is produced by Neuromedical Systems, Inc. ® of Suffern, New York under trademark PAPNET ™.

SUMMARY OF THE INVENTION

The present invention provides a method and apparatus for automating a cell classification process using at least primary and secondary classifications. Specifically, the primary classification step includes performing morphological filtering on an image of a biological specimen to detect cells having certain morphological features, such as a generally round shape or a certain size. The secondary classification step then further classifies these objects using an implementation of a neural network. The present invention preferably performs at least two scans of the specimen to produce one image suitable for analysis by the primary and secondary classifiers and a second image suitable for display on a high resolution color monitor to facilitate inspection by a cytotechnician.

In accordance with the present invention, a method of classifying cells based upon their morphology includes a method of classifying objects in a cytological specimen, including the steps of obtaining a first image of at least part of a cytological specimen, classifying objects in the first image on the basis of a predetermined criteria, obtaining a second image of at least one of the objects most likely to have a predetermined criteria, and displaying at least part of the second image to produce a visual display of at least one of the objects most likely to have a predetermined criteria.

In accordance with another aspect of the invention, a method of classifying objects in a specimen includes the steps of obtaining a first digital representation of at least part of the cytological specimen, storing the first digital representation, performing a first filtering operation to filter out images in the representation that are the approximate size of a malignant or premalignant cell or smaller to produce a second digital representation, removing the images in the second representation from the images in the first representation to produce a third representation, performing a second filtering operation to filter out images in the first representation that are the approximate size of a premalignant or malignant cell or larger than the approximate size of a premalignant or malignant cell to produce a fourth representation, and eliminating the images in the fourth representation from the images in the third representation to produce a representation having substantially only images the approximate size of a premalignant or malignant cell.

In accordance with a further aspect of the invention an apparatus for classifying objects in a cytological specimen includes a device for obtaining a first image of at least part of the cytological specimen, a processor for classifying objects in the first image on the basis of a predetermined criteria, a device for obtaining a second image of at least one of the objects most likely to have a predetermined criteria, and a monitor for displaying at least part of the second image to produce a visual display of at least one of the objects most likely to have the predetermined criteria.

These and other objects, advantages, features and aspects of the present invention will become apparent as the following description proceeds.

To the accomplishments of the foregoing and related ends, the invention, then comprises the features hereinafter fully described in the specification and particularly pointed out in claims, the following description and the annexed drawings setting forth in detail a certain illustrative embodiment of the invention, this being indicative, however, of but one of the various ways in which the principals of the invention may be employed. It will be appreciated that the scope of the invention is to be determined by the claims and the equivalents thereof.

DETAILED DESCRIPTION OF THE INVENTION

Figure 1:
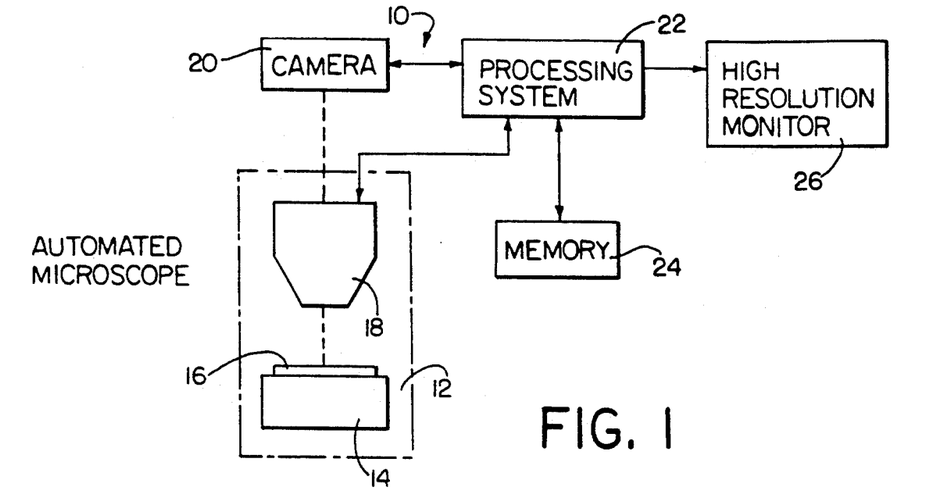
FIG. 1 is a schematic illustration of a cytological classification or screening device in accordance with the present invention.

With reference to the several figures in which like reference numerals depict like items, and initially to FIG. 1, there is shown an automated cell classification device 10 in accordance with the present invention. Briefly, the device 10 includes an automated optical microscope 12 having a motorized stage 14 for the movement of a slide 16 relative to the viewing region of the viewing portion 18 of the microscope, a camera 20 for obtaining electronic images from the optical microscope, a processing system 22 for classifying objects in the images as likely to be of a predetermined cell type, and a memory 24 and a high resolution color monitor 26 for the storage and display respectively of objects identified by the processing system as being likely to be of that predetermined cell type.

In its preferred embodiment the classification device 10 is completely, or nearly completely, automated. As such the microscope 12 will preferably include, in addition to the motorized stage 14, automated apparatus for focusing, for changing lens objectives between high and low power, and for adjustment of the light incident of the slide, as well as circuitry for controlling the movement of the motorized stage, typically in response to a command from the processing system. The microscope may also include an automated slide transport system for moving the slides containing the specimen to be classified on to and off of the motorized stage, a cell dotter for marking relevant areas of the slide, and a bar code reader for reading encoded information from the slide. An example of an automated microscope performing at least some of these functions is manufactured by McBain Instruments of California.

Figure 2:
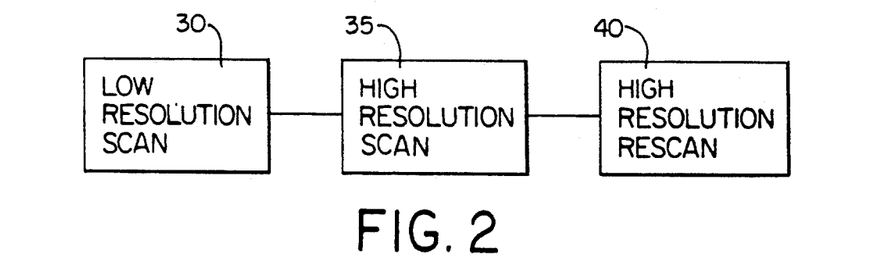
FIG. 2 is a diagrammatic illustration of the scanning passes which the screening device performs.

In accordance with the invention the automated microscope 12 preferably performs three scans of the slide having the specimen disposed thereon, as shown diagrammatically in FIG. 2. The first scan of the slide is performed at a relatively low magnification, for example 50 power, and is called the low resolution scan (30). The second scan is performed at a higher magnification, for example 200 power, and is called the high resolution scan (35). The third scan is referred to as the high resolution rescan and is also performed at a high magnification (40).

During the first scan (30) of the slide, approximate focal planes for the specific areas of the slide are found and it is determined whether that area of the slide contains a portion of the specimen. Once a low resolution scan (30) has been performed of the whole slide, and the focal planes and areas of the slide containing the specimen have been logged, the high resolution scan (35) is performed.

The high resolution scan (35) is performed only on the areas of the slide found in the low resolution scan (30) to contain a portion of the specimen. Consequently, the comparatively long high resolution scan (35) is performed only on relevant areas of the slide and the processing time is greatly reduced. During the high resolution scan (35), the automated microscope 12 scans the relevant areas of the slide, and the camera 20 takes electronic images of these areas and sends the images to the processing system 22. The processing system performs a primary classification of the image which finds the centroids of biological objects having attributes typical of the cell class for which screening is being performed, such as malignant cells. Using a smaller sub-image centered around these centroids, the processing system 22 performs a secondary classification which assigns each centroid a value indicative of the possibility that the object having that centroid is a cell of the type for which classification is being performed. Simultaneously, the centroids are also ranked based on the value assigned through the secondary classification.

Upon completion of the high resolution scan (35), the high resolution rescan (40) is performed for the highest 64 ranked objects. During the rescan (40) the automated microscope 12 will move to each of the highest 64 ranked centroids and the camera 20 will obtain a high resolution color image of the object having that centroid. These 64 high resolution images, called color tiles, are then stored in the memory 24 which may be a removable device, such as an optical disk or a tape, etc., or a fixed storage device such as a hard disk. Alternatively, the sixty-four color tiles may be transferred to another computer via a network or through transportation of the data on a removable storage media.

The sixty-four color tiles make up a summary screen which is preferably an 8×8 matrix of high resolution color tiles featuring a suspect cell in the center of each tile. It will be appreciated, however, that other numbers of color tiles may be displayed concurrently to produce a summary screen, such as a 4×4 matrix. These summary screens are displayed on the high resolution color monitor 26 for tertiary analysis and classification by a cytotechnician. This analysis may take place at anytime after the highest sixty-four have been secondarily classified and ranked. Further, through the use of a removable memory device or a network connection, the images and tiles of the summary screen may be transferred to a workstation remote from the microscope 18, camera 20 and processing system 22 for display and analysis. In such an instance a separate graphics processor 41 (FIG. 3) may be employed to drive the high resolution color monitor 26 and provide a suitable interface with the cytotechnician.

A cytotechnician or cytotechnologist (hereinafter cytotechnician) can easily scan the summary screen in search of an object having the attributes of the cell type for which classification is being performed. If the system is being used to screen a pap smear for the presence of cervical cancer, the cytotechnician would typically look for cells having attributes of malignant or premalignant cervical cells, such as a comparatively large, dark nucleus. The cytotechnician may also make a determination from the summary screen as to whether a specimen having no malignant or premalignant cells was taken properly. This can be done by ascertaining the presence of endocervical cells. Endocervical cells make up the lining of the transitional zone of the cervix where most cervical cancers start; consequently, their presence in a pap smear specimen indicates that the test swab must have made contact with the critical transitional zone of the cervix. Since endocervical cells have more characteristics common to a malignant cell than a vaginal or other benign cell has, in the absence of any true premalignant or malignant cells it will be ranked above the other cells and displayed.

Herein the screening method and apparatus of the present invention will be described as used in screening a pap smear for the presence of cervical cancer cells. However, it will be apparent to a person of ordinary skill in the art that this is only an illustrative use and that the present invention may be used in screening samples of other biological matter taken by a variety of cell sampling techniques, such as aspiration and exfoliation to name but two. Further it will be apparent that while the illustrative example screens for malignant or premalignant cells, the screening may be performed for the detection of other cell classes or types.

Figure 3:
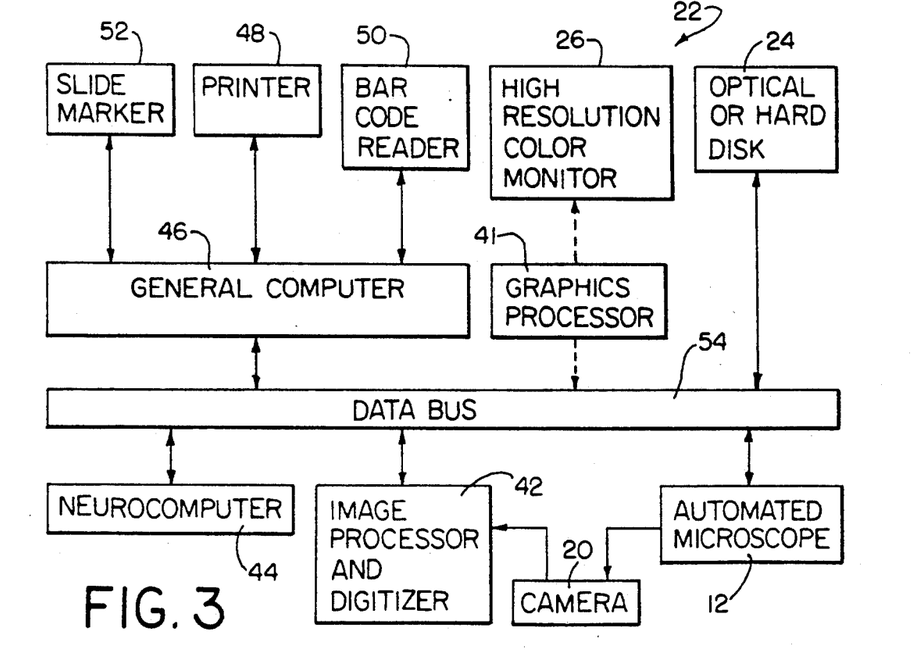
FIG. 3 is a schematic illustration of the screening device of FIG. 1 with particular emphasis on the processing system.

Turning now to a more in-depth discussion of the present invention with specific reference to FIG. 3, the screening device 10 is shown with particular emphasis on the classification elements embodied in the processing system 22. The processing system 22 preferably includes an image processor and digitizer 42, a neurocomputer 44, and a general processor 46 with peripherals for printing, storage, etc.

The general processor 46 is preferably an Intel ® 80386 microprocessor or faster microprocessor based microcomputer although it may be another computer-type device suitable for efficient execution of the functions described herein. The general processor 46 controls the functioning of and the flow of data between components of the device 10, may cause execution of additional primary feature extraction algorithms and handles the storage of image and classification information. The general processor 46 additionally controls peripheral devices such as a printer 48, a storage device 24 such as an optical or magnetic hard disk, a tape drive, etc., as well as other devices such as a bar code reader 50, a slide marker 52, autofocus circuitry, a robotic slide handler, and the stage 14.

The image processor and digitizer 42 performs the primary cell classification functions described more fully below. In the preferred embodiment, the image processor and digitizer 42 is a commercially available low level morphological feature extraction image classifier such as the ASPEX Incorporated PIPE ® image processor which includes among other things an image digitization function and an ISMAP (Iconic to Symbolic Mapping) board. The PIPE ® image processor is described more fully in U.S. Pat. No. 4,601,055, the entire disclosure of which is incorporated by this reference. Alternatively, the image processing and digitization functions could be separated into two or more components. Below, the image processor and digitizer will be conjunctively referred to as the image processor 42.

Secondary cell classification is performed by the neurocomputer 44. The neurocomputer 44 is a computer embodiment of a neural network trained to identify suspect cells. In this embodiment the parallel structure of a two or three-layer backpropagation neural network is emulated with pipelined serial processing techniques executed on one of a host of commercially available neurocomputer accelerator boards. The operation of these neurocomputers is discussed in Hecht-Nielsen, Robert, "Neurocomputing: Picking the Human Brain", IEEE Spectrum, March, 1988, pp. 36–41. The neural network is preferably implemented on an Anza Plus TM processor, which is a commercially available neurocomputer of Hecht-Nielsen Neurocomputers. Such a neurocomputer could be easily configured to operate in a manner suitable to perform the secondary classification functions by one of ordinary skill in the art through reference to corresponding manuals, etc. Alternatively, secondary cell classification functions could be performed using a template matching algorithm designed to identify shapes known to be typical of a pathological cell. A template matching or other group processing algorithm could be efficiently implemented in a parallel distributed processing network, for example. Another alternative secondary classification embodiment is a holographic image processor designed to perform group based classification.

The image processor 42, the neurocomputer 44, and the general computer 46 may each access read-only and/or random access memory, as would be readily apparent to one skilled in the art, for the storage and execution of software necessary to perform the functions described relative to that processing component. Further, each component 42, 44, 46 includes circuitry, chips, etc. for the control of communication or data transfer over the data bus 54 as well as other functions typical of similar processors as would be appreciated.

Figure 4:
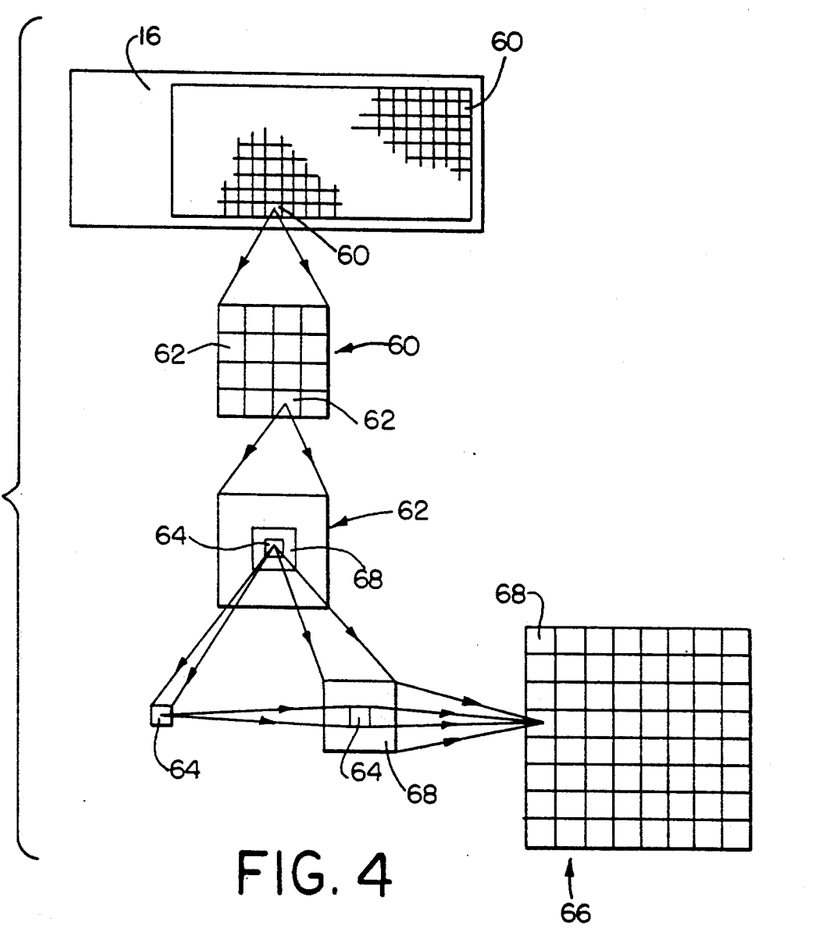
FIG. 4 is an illustration of the various image components representing areas of the specimen.

Returning to a discussion of the operation of the device 10 and with reference to FIG. 4, the area of the slide 16 possibly containing the biological matter of the specimen is segmented into a plurality of rows and columns, for example, 20 rows and 50 columns of equal sized blocks 60. Each block 60 occupies an area of the slide, for example, approximately 2000 microns × 1600 microns, and corresponds to an individual image to be viewed one by one by the microscope. Each block 60 is subdivided, for example, into sixteen equally sized analysis fields 62. Each field 62 is thus approximately 500 microns by 400 microns in size. Once digitized by the image processor 42, each analysis field 62 will be represented by a 256 by 242 matrix or array of pixels which corresponds to a resolution of approximately two microns per pixel during a low resolution scan (30) or high resolution scan (35), or a 512 by 484 array of pixels corresponding to a one micron per pixel resolution during a high resolution rescan pass (40). Each pixel then represents the brightness, or gray scale density of a discrete area of the analysis field 62 image. The gray scale density of each pixel is further represented by an 8 bit digital value. Consequently, each pixel will represent an area of the analysis field image 62 by a gray scale level ranging from zero to 255. In operation, the screening device will perform a low resolution scan (30) on each analysis field 62 to determine if that field contains biological matter, and a high resolution scan (35) on each of the analysis fields 62 having biological matter to detect objects contained therein which are likely to be malignant or premalignant cells. A third scan (40), the high resolution rescan, may also be performed on an analysis field 62, or a portion of an analysis field, if during the high resolution scan (35) the processing system found an object within the field which is likely to be a malignant or premalignant cell.

During the low resolution scan (30) the objective of the microscope 12 is set, for example, at its 50 magnification power, and the microscope begins scanning the individual blocks 60 of the slide 16. For each block 60 the microscope 12 will automatically determine the approximate focal plane for that area of the slide 16. As the cover slip covering the specimen tends to be somewhat wavy or possibly angled, such as due to air bubbles contained under the cover slip, the focal plane may vary from block 60 to block. Once the focus is determined for the block 60 being viewed, the camera 20 will capture the image of the block and send that image to the image processor 42 through a suitable digitizer. The image processor 42 then subdivides the block 60 into analysis field 62 and determines whether there are areas of interest in each analysis field corresponding to objects which may be biological material. If a field 62 contains material which may be biological, the block 60 is identified along with its approximate focal plane and stored in memory for future analysis during the high resolution scan (35). This low resolution scan (30) should be performed for all blocks 60 on the slide 16.

Once the low resolution scan (30) has been completed and all of the blocks 60 containing objects which are possibly biological material have been identified in memory, the high resolution scan (35) is begun. Initially, a scan path is determined which will allow the microscope 12 to view each block 60 possibly containing biological matter preferably with the least amount of movement of the slide 16. For the high resolution scan (35), the objective corresponding, for example, to a 200 power magnification is inserted into the viewing path of the microscope 12, and the scan is begun at the first block 60 in the scan path. The microscope 12, via the motorized stage 14 will move the slide 16 into a position such that the first block 60, which was identified as having biological material during the low resolution scan, will be in the field of view of the microscope. The microscope 12 will then, based initially on the focal plane determined during the low resolution scan (30), focus the block 60 under the high resolution magnification level. The block 60 is digitized and again subdivided into 16 analysis fields 62. The image processor 42 will then perform the primary classification of the objects in each analysis field 62 as discussed more fully below. This primary classification finds the centroids of objects in each field that have the correct size and gray scale density characteristics.

When an object in an analysis field 62 has been identified as having the size and gray scale density characteristics of a premalignant or malignant cell, a 24×24 array of pixels surrounding the object centroid, called a net image 64, is transferred to the secondary classifier for further classification. A net image 64 is approximately 48×48 microns in size at a resolution of 2 microns per pixel. As a malignant or premalignant cell nucleus tends to range between 10 and 40 microns in diameter, the net image 64 is sufficiently large to contain a complete image of a suspect cell.

The highest 64 ranked objects are displayed on the summary screen 66. As discussed above, the summary screen may be an 8×8 matrix of 64 discrete images, called color tiles 68, a 4×4 arrangement of 16 color tiles, or some other arrangement. Color tiles 68 are obtained during the rescan pass (40). Each color tile represents an approximately 128×104 micron area surrounding the centroid of a suspect cell, with a resolution of one micron per pixel. Each color tile produces a high resolution color image of a suspect cell and surrounding cells and biological matter, with the suspect cell centered in the tile. By reviewing the summary screen 66, the cytotechnician can relatively easily classify the high resolution color images of the suspect cells.

It will be appreciated by a person of ordinary skill in the art that while particular resolutions and image sizes were described above, these particular values are exemplary. It will further be appreciated that different resolutions, image parameters, magnification levels, etc., can be employed to accomplish the same or similar results as the particular embodiment of the invention described above, and that all such differing resolutions, image parameters, etc. are within the scope of the present invention.

Figure 5A:
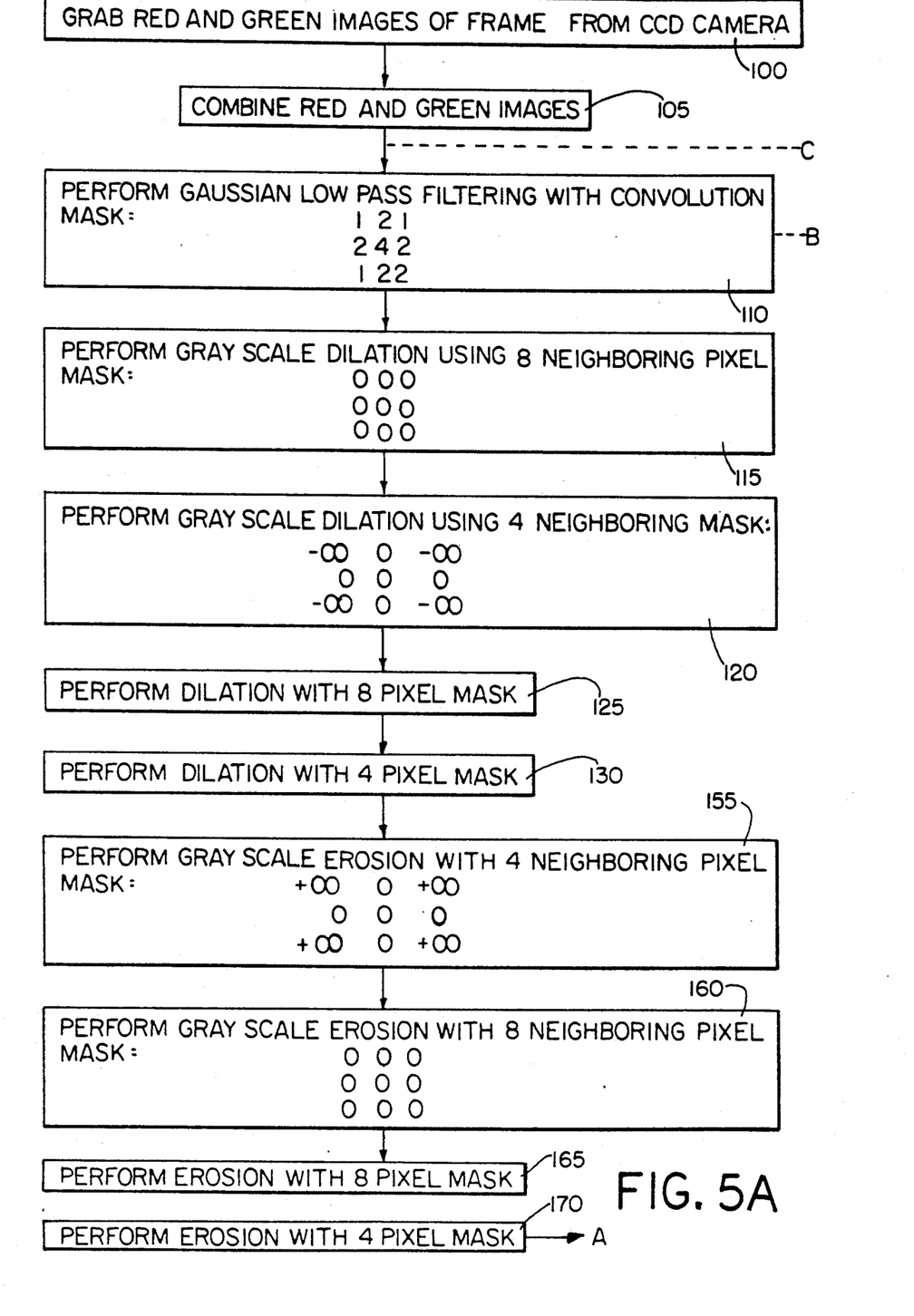
FIGS. 5a through 5c are flowcharts illustrating the primary classification function of the present invention.
Figures 5B, 5C:
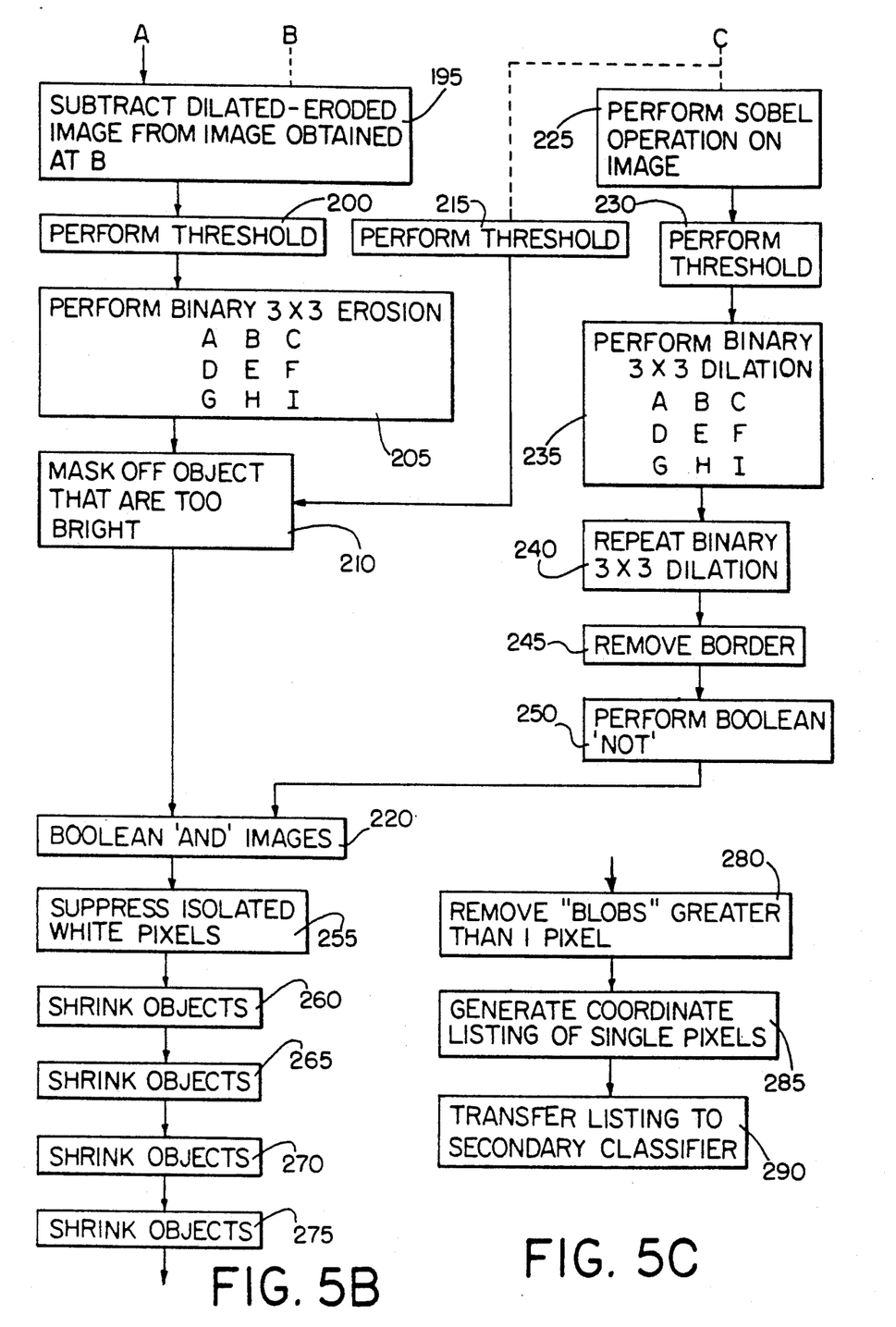

Turning to a more in-depth discussion of the primary classification routine, and referring to FIGS. 5a-5c, there is shown a flowchart of the primary classification functions which the image processor 42 performs. Numbers contained within parenthesis below correspond to like numbered steps in the flowchart. Similarly, letters contained within parenthesis denote the flow of image data at various steps in the flowchart. Once a block image 60 has been focused and taken by the camera 20, the image processor 42 will digitize an area of the block 60 corresponding to an analysis field 62 and grab the 8 bit gray scale red and green images from the camera (100). The red and green 8 bit gray scale images are then combined to produce a monochrome image (105) which is stored in a segment of memory of the image processor 42, called the frame buffer. The Papanicolaou stain used in treating a pap smear dyes the nuclei of biological cells within the smear a purple color. Since the colors red and green when combined approximately equally make a yellowish green color which is directly opposite the color purple on a color space triangle, combining red and green, without blue, creates an image wherein the purple stained nuclei appear very dark and the areas of other colors appear brighter.

Briefly, the primary classifier performs a morphological "well" algorithm which filters out objects that are the size of a premalignant or malignant cell or smaller. (A "well" algorithm is the inverse of a morphological "top hat" algorithm.) The resulting image, containing only objects which are too large to be a cancerous cell, is then subtracted from the original image containing all of the objects. Consequently, what is left are objects of the correct size or smaller. A separate image is then prepared from the original image which will contain only objects which are too small to be of concern. When this latter image, containing only objects which are too small, is then subtracted from the image having objects of the size of a possible cancerous cell or smaller, the resultant image will thus contain only images being of the size of a possible cancerous cell. The centroids of the objects in this image are then determined and the images centered around those centroids are sent to the secondary classifier for further classification.

The image in the frame buffer, which corresponds to an analysis field 62 and is referred to herein as the frame image, is spatially filtered such as with a gaussian low pass filter to remove random noise from the image (110). Preferably, the gaussian filter has a convolution mask of:

| 1 | 2 | 1 |
|---|---|---|
| 2 | 4 | 2 |
| 1 | 2 | 1 |

This convolution mask is moved across every pixel in the frame image. To explain, the convolution mask will be initially centered on the first pixel in the frame image pixel matrix. Consequently, the 8 bit gray value of this pixel will be multiplied by 4 while the 8 bit gray values of the pixels immediately above and below and on either side will be multiplied by 2, and the adjacent diagonal pixels will have their 8 bit gray scale values multiplied by 1. All nine of these results are summed and the result is divided by 16 and placed in a pixel location in a result frame corresponding to the location of the center pixel. The convolution mask is then shifted to the next pixel in the frame image pixel matrix and the operation is repeated. This continues for all pixels in the matrix, thus generating a complete result frame.

A morphological closing is then performed on the frame image in the result frame to filter out all objects smaller than a certain diameter which is somewhat larger than the size of a malignant cell nucleus. Consequently, what is left are only those objects which are too large to correspond to malignant cell nuclei. This morphological closing is performed using a series of gray scale dilation operations followed by a series of gray scale erosion operations. Gray scale dilation is a mathematical morphology term used in image processing to denote an operation wherein a mask is centered on a pixel and a corresponding pixel in a corresponding result frame pixel is replaced by the largest value of its neighboring pixels added to their corresponding mask values or itself added to its corresponding mask value. Erosion is a similar term wherein the center pixel is replaced by the minimum value of its neighbors added to their corresponding mask values or itself with its corresponding mask value added to it.

In the preferred embodiment of the invention, gray scale dilation operations are performed using an 8 neighboring pixel mask wherein the center pixel and its 8 neighboring pixels are each allocated equal weights, followed by a gray scale dilation using a 4 neighboring pixel mask wherein the pixels diagonally related to the center pixel are ignored and the remaining 4 neighboring pixels are allocated equal weights with the center pixel. The respective masks for these dilation operations would appear as:

| 0 | 0 | 0 | $-\infty$ | 0 | $-\infty$ |
|---|---|---|---|---|---|
| 0 | 0 | 0 | 0 | 0 | 0 |
| 0 | 0 | 0 | $-\infty$ | 0 | $-\infty$ |

For the erosion operations, a gray scale erosion operation is first performed using a 4 neighboring pixel mask followed by an erosion using an 8 neighboring pixel mask where all the neighboring pixels are taken into account. The respective masks for the erosion operation would appear as:

| $+\infty$ | 0 | $+\infty$ | 0 | 0 | 0 |
|---|---|---|---|---|---|
| 0 | 0 | 0 | 0 | 0 | 0 |
| $+\infty$ | 0 | $+\infty$ | 0 | 0 | 0 |

The combination of operations using these masks morphologically approximates an octagon, which is digitally analogous to the morphology of a nucleus which tends to be generally round.

Figure 6A:
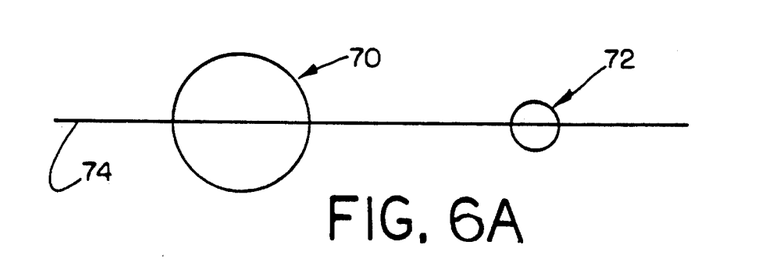
FIGS. 6a through 6d are graphical representations of a morphological closing operation performed during the primary classification function.
Figure 6B:
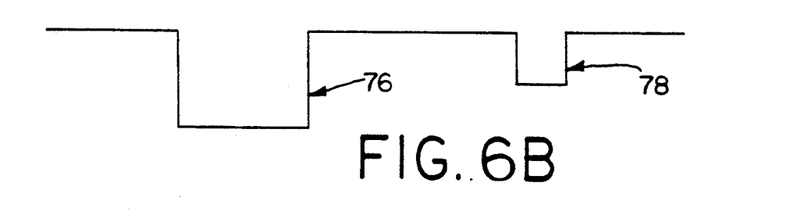

The manner in which this morphological closing filters small objects out of the image is graphically represented in FIGS. 6a–d. FIG. 6a illustrates two objects; the object on the left 70 is a large dark nucleus and the object on the right 72 is a smaller, less dark cell, such as a leukocyte. The horizontal line 74 represents a row of pixels passing through the objects 70, 72. The gray scale values for this row of pixels is shown in FIG. 6b. The large dark nucleus 70 forms a wide and deep gray scale rectangle 76 due to its relatively large size and darkness. The leukocyte 70, being smaller and less dark, forms a narrower, shallower rectangle 78.

Figure 6C:
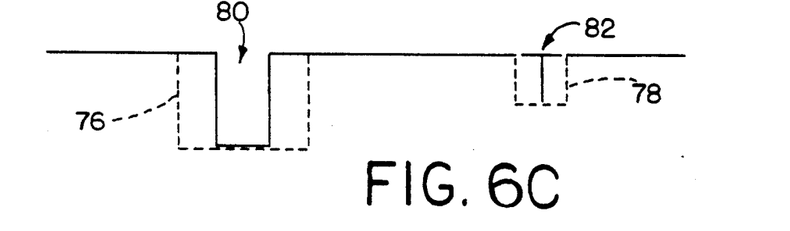
Figure 6D:
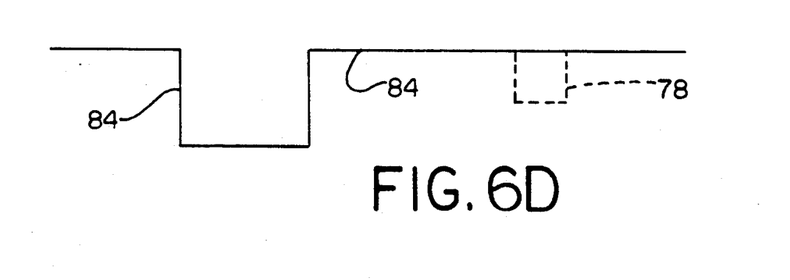

As dilation operations are performed, these gray scale rectangles are gradually filled in as indicated in FIG. 6c. After one such dilation operation, the large dark nucleus may now be represented by the relatively wide depression 80 while the leukocyte may be represented by the narrow spike 82. Subsequent dilation operations will continue to fill in these depressions. Consequently, a relatively small object will be completely filled in while larger, darker objects, such as malignant nuclei, will remain as somewhat narrower depressions.

When the image is then subjected to a series of erosion operations, the narrow depressions which are the gray scale representations of large, dark objects will be expanded to approximately their original size and shape, whereas the completely filled in gray scale representations of small objects will not be eroded. The morphological closing will thus yield a row of pixels having gray scales, as shown by the solid line 84 in FIG. 6d, which represent the large dark object, but have the object which is too small to be a malignant or premalignant cell.filtered out.

A discussion of mathematical morphology can be found in Sera, "Introduction to Mathematical Morphology" Computer Vision, Graphics, and Image Processing, 35, 283–305 (1986) and Steinberg, "Grayscale Morphology", Computer Vision, Graphics, and Image Processing, 35, 333–355 (1986).

Returning to the flowchart illustrated in FIGS. 5a–5c, a gray scale dilation is performed on the gaussian low pass filtered frame image using an 8 neighboring pixel mask (115). A gray scale dilation is then performed on this dilated frame image using a 4 neighboring pixel mask (120). This series of gray scale dilations is then performed one additional time (125, 130).

The dilated image is then eroded using a 4 neighboring pixel mask erosion followed by an 8 neighboring pixel mask erosion (160). Again, this series of erosions is performed one additional time (165, 170).

It will be appreciated by a person skilled in the art that other filtering functions could be performed to achieve similar results, such as a rolling ball or cone filter.

The resulting dilated-eroded frame image has now had the smaller objects filtered out and consists only of objects which are larger than a malignant cell nucleus. This dilated eroded frame image is then subtracted from the frame image (B) which has been gaussian filtered but not dilated and eroded (195). The resultant frame image thus consists only of objects which generally correspond to the size of a malignant or premalignant nucleus or smaller.

A threshold operation is then performed on this image with pixels having a gray scale value above a certain threshold being assigned a binary '1' and those pixels have gray scale values below that threshold being assigned a binary zero (200). The threshold is chosen to filter out objects which are not dark enough to be nuclei. A binary 3×3 erosion is then performed on the image to remove the outer pixel boundary of the remaining objects, thus making the objects narrower by one pixel in all directions (205). This binary erosion is accomplished by performing a boolean AND on the center pixel and the eight neighboring pixels. Representing the mask as below:

|   |   |   |
|---|---|---|
| A | B | C |
| D | E | F |
| G | H | I |

Mathematically, this will be represented as A and B and C and D and E and F and G and H and I, where each letter indicates a binary value at certain pixel locations. As discussed above relative to the gaussian low pass filter, dilation and erosion operations, this mask slides across the frame so that the binary erosion is performed with the mask eventually centered on each pixel in the frame, thus creating an eroded result frame image.

The resulting image is then boolean ANDed (210) with the original frame image (C) which has been thresholded (215) as described above to produce a binary image. Boolean ANDing these images masks off objects that are of the appropriate size but are too bright to be malignant or premalignant cervical cells. An example of the objects which would be eliminated from the frame image by this operation are clumps of red blood cells.

The frame image now contains objects of the appropriate gray scale density that are of a size corresponding to a malignant or premalignant cervical cell and smaller. These smaller objects typically represent neutrophils which are white blood cells. Consequently, these objects which are smaller than a cancerous cervical cell nucleus must be removed from the frame image. Since the frame image is now in a binary format, a binary mask is needed to mask off the smaller objects. Accordingly, the mask would have binary '1''s in all locations of the frame image pixel array except for those locations occupied by a small image, where there would be zeros. Consequently, by boolean ANDing the binary frame image with the binary mask the small objects are removed and predominantly what is left are objects of the appropriate gray scale density and size for a cervical cancer cell nucleus (220).

This mask is obtained by taking the untreated frame image (C) stored earlier and treating the image with a well-known Sobel operator to find areas within the image (225) having relatively large arithmetic gradients. Areas of high detail in the image, or areas having relatively small objects, will have large gradients. The Sobel operator, which is essentially a high-pass image filter, will pass those areas having large gradients and reject the areas of large objects which have smaller gradients. By choosing the correct filter parameters, the edges of objects are found. The image is then thresholded to convert the gray scale image into a binary image (230). A 3×3 binary dilation is then performed on the image to slightly expand or thicken the edges in the image (235). The binary dilation operation is performed as a boolean 'OR' operation. Using the mask notation discussed earlier relative to binary erosion, mathematically the binary dilation would be expressed as A|B|C|D|E|F|G|H|I. The dilation operation is then repeated preferably using only the adjacent pixels. Mathematically this second dilation would be represented as B|D|E|F|H (240). After the edge thickening operation, objects smaller than a certain diameter will have become solid "blobs" and objects larger than this diameter will remain open in the center. This function could also be performed with a gray-scale morphological well or top hat filter as described above with its parameters set to find smaller objects.

A number of the outermost rows and columns of pixels, for example, eight, forming a border around the frame are then removed, as they contain artifacts and other irrelevant information introduced by the operations performed above (245). The complement of the resultant image is then taken by a boolean 'NOT' operation (250). Consequently, the binary image will consist of binary '1''s in all locations except in the slightly enlarged areas encompassing objects too small to be malignant cells. This complemented image thus forms the binary mask used to subtract the small objects from the earlier developed frame image. When boolean ANDed with the frame image having objects of the appropriate size and smaller (220), the small objects will be eliminated.

Once the small objects have been removed and the frame image contains predominantly objects having a gray scale density and size compatible with the gray scale density and size of a cervical cancer cell nucleus an operation is performed to suppress isolated white pixels in the frame image (255). These isolated white pixels (binary '1') constitutes noise introduced during any of the previous operations and are not of a sufficient size to be a cell nucleus. Using the binary mask notation discussed above relative to binary erosion and dilation operations, the suppression operation can be expressed mathematically as (E and A)|(E and B)|(E and C)|(E and D)|(E and F)|(E and G)|(E and H)|(E and I).

Once the isolated pixels have been suppressed, a "shrinking" operation is performed four times (260, 265, 270, 275). "Shrinking" is a boolean operation well-known in the field of image processing. The shrinking operation successively removes layers of pixels around the object in the image frame until, for an object of the appropriate size, only one pixel or no pixels remain. In the case where the object is completely removed, the last pixel removed is replaced with a binary 1. Since the outer layers of pixels of the objects were successively removed progressing inwardly, the remaining or replaced pixel will represent the approximate center or centroid of the object. Any objects remaining in the image which are larger than one pixel are removed, as they correspond to something which is larger than a cervical cancer cell nucleus would be (280).

The location of the remaining single pixels, as defined by their X and Y coordinates on the screen, are then listed and recorded in memory (285). The ISMAP board of the PIPE® image processor conveniently provides these coordinates. The identification of the centroids of objects which correspond to the same size and gray scale density that a typical cervical cancer cell would be expected to have marks the end of the primary classification phase of operation.

Given the discussion above and a general knowledge of image processors, such as the preferred PIPE® image processor, the primary classification functions could be reduced to the appropriate software code for execution on a suitable image processor. As would be apparent, the code would be loaded, burned, or otherwise encoded into memory accessible by the image processor 42 for execution by the image processor.

A 24×24 array of pixels surrounding each centroid, identified earlier as a net image 64, identified by the primary classification function of the image processor 42 is then transferred to the general processor 46 for storage. A secondary classification of the objects represented by these net images 64 may then be performed.

The general processor 46 individually transfers each net image 64 to the neurocomputer 44 for secondary classification. The task of the secondary classification is to distinguish the premalignant and malignant cells from other objects of the same size which may pass the primary classifier, such as cell clumps, debris, clumps of leukocytes and mucus.

Based on training performed with a training set of several hundred or thousands of known benign and premalignant or malignant cells, as described more fully above, the neurocomputer 44 will assign each net image 64 with a value, called a net value, ranging from 0.1 to 0.9, as determined by the likelihood that the object is a premalignant or malignant cell. One major advantage of the present invention over prior known cell classifiers resides in the fact that each net image 64 presented to the secondary classifier is precentered through the primary classification on the centroid of the suspect cell nucleus, as described above. In previous known attempts to utilize neural networks and other high level template matching pattern classifiers for image recognition, difficulty has been encountered in consistently presenting the classifier with the centroid of the image requiring classification. To use an example from another application domain, back propagation networks are excellent at reading handwritten zip code digits but have difficulty in finding where the zip code is on the envelope. The present invention overcomes this difficulty in the domain of cytology.

Another advantage of the present invention is that during actual classification operations, a secondary classifier is presented with precisely the same type of net images on which it was trained. These images are also centered on the centroid of the suspect nucleus by the primary classifier in a manner identical to that used to prepare the training set images. This makes a generalization task of the secondary classifier far easier and much more successful than anything previously known.

It should be recognized that while the image processor and digitizer 42, the general processor 46, and the neurocomputer 44 are described operating in a serial manner, in actual practice as many functions will be performed in parallel as is possible. Consequently, the components 42, 44, 46 may process different slide segments or different areas of a segment concurrently, greatly reducing the time required to screen a slide.

As noted above the secondary classifier is trained to associate a known benign image with an output of 0.1 and a known pathological image with an output of 0.9. Such outputs represent, for example, the degree of certainty that a cell is normal or abnormal, respectively. When the secondary classifier is presented with new, unknown cells, it generalizes from its training and attaches a net value to the image. The closer that the secondary classifier is able to categorize the unknown image into the benign category, the closer is its net value equal to 0.1. Conversely, the more closely that the unknown image appears to resemble the nonbenign images of its training set, the closer is the net value assigned to that image equal to 0.9.

Once all objects classified by the primary classifier to be possibly premalignant or malignant have been classified by the secondary classifier, the net values assigned to those objects by the secondary classifier are ranked from closest to 0.9 down to 0.1. The highest ranked 64 objects are then stored. This completes the end of the high resolution scan (35).

Once the highest ranked 64 objects in the specimen have been identified which are most likely to be malignant or premalignant, the high resolution rescan (40) is begun at the 200 power magnification. During the rescan (40) the stage 14 will move the slide relative to the microscope 12 so that one of the highest 64 ranked object is in the viewing path of the microscope. The image is then focused according to the previously determined high resolution focus parameters, and the camera grabs, at 512×484 resolution, the 128×104 red, green and blue component image around the centroid location. This high resolution color tile 68 is then stored in the memory 24, such as on an optical disk or tape. These operations are then performed for the next cell until all 64 of the highest ranked cells have been rescanned and their high resolution color images have been stored in the memory 24. This completes the rescan pass (40). The automated classifier 10 may then remove the slide and replace it with another slide for further classification.

Once stored, the 64 color tiles 68 may be displayed as a summary screen 66 in their descending order of ranking, their positioned relation to each other in the specimen, or in some other arrangement. The tertiary classification performed by a cytotechnician can then take place at any time.

STATEMENT OF INDUSTRIAL APPLICATION

The present invention is applicable to cell classification in general and is particularly applicable to the classification of cells in a pap smear.

What is claimed is:

1. A method of classifying objects in a cytological specimen, comprising the steps of:
    a) obtaining a first image of at least part of such cytological specimen;
    b) classifying objects in such first image on the basis of a predetermined criteria;
    c) selecting at least one object for display based on said classifying;
    d) obtaining a second image of at least part of such cytological specimen containing said at least one selected object; and
    e) displaying at least part of such second image to produce a visual display of said at least one selected object.

2. The method of claim 1, wherein such first image is of a lower resolution than such second image.

3. The method of claim 1, including the step of further classifying such objects in such visual display.

4. The method of claim 1, wherein such visual display represents plural objects.

5. The method of claim 4, including the step of arranging such plural objects in such visual display in an eight by eight array of sixty-four elements.

6. The method of claim 5, wherein a centroid of each object displayed is approximately centered in one of such elements.

7. The method of claim 5, wherein such plural objects are arranged in an order related to the likelihood that each object has such predetermined criteria.

8. The method of claim 5, wherein such plural objects are arranged according to their relative positional locations in such cytological specimen.

9. The method of claim 4, including the step of arranging such plural objects in such visual display in a four by four array of sixteen elements.

10. The method of claim 9, wherein a centroid of each object displayed is approximately centered in one of such elements.

11. A method of classifying objects in a cytological specimen; comprising the steps of:
   a) obtaining a first digital representation of at least part of such cytological specimen;
   b) storing such first digital representation;
   c) performing a first filtering operation to filter out images in such representation that are the approximate size of a malignant or premalignant cell or smaller to produce a second digital representation;
   d) removing the images in such second representation from the images in such first representation to produce a third representation;
   e) performing a second filtering operation to filter out images in such first representation that are the approximate size of a premalignant or malignant cell or larger than the approximate size of premalignant or malignant cell to produce a fourth representation; and
   f) eliminating the images in such fourth representation from the images in such third representation to produce a representation having substantially only images the approximate size of a premalignant or malignant cell.

12. The method of claim 11, wherein said step of performing a first filtering operation includes performing a morphological well function.

13. The method of claim 11, wherein said step of performing a first filtering operation, includes performing a morphological top hat function.

14. The method of claim 11 wherein said step of performing a second filtering operation includes performing an arithmetic gradient operation on such first digital representation.

15. The method of claim 14, wherein said step of performing an arithmetic gradient operation includes performing a Sobel operation.

16. The method of claim 11 wherein said step of performing a second filtering operation includes performing a morphological well function on such first digital representation.

17. The method of claim 11 wherein said step of performing a second filtering operation includes performing a morphological top hat function on such first digital representation.

18. The method of claim 11, wherein said step of removing includes masking out images which are too bright to be malignant or premalignant cells.

19. The method of claim 11, wherein said step of eliminating includes taking the complement of said fourth representation and boolean ANDing the resulting representation with such third representation.

20. The method of claim 19, wherein said step of taking the complement includes performing a boolean NOT.

21. An apparatus for classifying objects in a cytological specimen, comprising:
   means for obtaining a first image of at least part of such cytological specimen;
   means for classifying objects in such first image on the basis of a predetermined criteria;
   means for selecting at least one object for display based on classification performed by said means for classifying:
   means for obtaining a second image of such cytological specimen containing said at least one selected object; and
   means for displaying at least part of such second image to produce a visual display of said at least one selected object.

* * * * *

REEXAMINATION CERTIFICATE (2872nd)

United States Patent [19]
Luck et al.

[11] B1 5,257,182
[45] Certificate Issued  May 7, 1996

[54] MORPHOLOGICAL CLASSIFICATION SYSTEM AND METHOD

[75] Inventors: Randall L. Luck, Brooklyn; Richard Scott, New York, both of N.Y.

[73] Assignee: Neuromedical Systems, Inc., Suffern, N.Y.

Reexamination Request:
No. 90/003,816, May 1, 1995

Reexamination Certificate for:
Patent No.: 5,257,182
Issued: Oct. 26, 1993
Appl. No.: 647,438
Filed: Jan. 29, 1991

[51] Int. Cl.⁶ ..................................................... G06F 18/00
[52] U.S. Cl. ..................... 364/413.1; 395/924; 382/133

[56] References Cited

U.S. PATENT DOCUMENTS

| | | |
|---|---|---|
| 3,824,393 | 7/1974 | Brain . |
| 4,122,518 | 10/1978 | Castleman et al. . |
| 4,175,860 | 11/1979 | Bacus . |
| 4,523,278 | 6/1985 | Reinhardt et al. . |
| 4,601,055 | 7/1986 | Kent . |
| 4,612,614 | 9/1986 | Deindoerfer et al. . |
| 4,700,298 | 10/1987 | Palcic et al. . |

OTHER PUBLICATIONS

Dytch et al., "An Interactive Microcomputer–Based System for the Quantitative Analysis of Stratified Tissue Sections", *Analytical and Quantitative Cytology and Histology*, vol. 9, No. 1, pp. 69–78 (The International Academy of Cytology Mar. 1987).

Erhardt et al., "FAZYTAN—A System for Fast Automated Cell Segmentation, Cell Image Analysis and Feature Extraction Based on TV–Image Pickup and Parallel Processing", *Analytical and Quantitative Cytology*, vol. 2, No. 1, pp. 25–40 (The International Academy of Cytology Mar.–Apr., 1980), presented at the 1979 International Conference on Pattern Recognition of Cell Images, Chicago, IL, May 21–23, 1979).

Reinhardt et al., "Structure Analysis and Classification of Cervical Cells Using a Processing System Based on TV", *Analytical and Quantitative Cytology*, vol. 1, No. 2, pp. 143–150 (The International Academy of Cytology, Jul.–Aug., 1979).

Meyer, "Automatic Screening of Cytological Specimens", *Computer Vision, Graphics, and Image Processing* 35, pp. 356–369 (Academic Press, Inc. 1986).

Pratt, *"Digital Image Processing"*, pp. 486–497, 500–512, (Wiley–Interscience, 1978).

(List continued on next page.)

*Primary Examiner*—Ruth S. Smith

[57] ABSTRACT

A method of classifying cells based upon their morphology includes a method of classifying objects in a cytological specimen, including the steps of obtaining a first image of at least part of a cytological specimen, classifying objects in the first image on the basis of a predetermined criteria, obtaining a second image of at least one of the objects most likely to have a predetermined criteria, and displaying at least part of the second image to produce a visual display of at least one of the objects most likely to have a predetermined criteria. The method of classifying objects in a specimen includes the steps of obtaining a first digital representation of at least part of the cytological specimen, storing the first digital representation, performing a first filtering operation to filter out images in the first representation that are the approximate size of a malignant or premalignant cell or smaller to produce a second digital representation, removing the images in the second representation from the images in the first representation to produce a third representation, performing a second filtering operation to filter out images in the first representation that are the approximate size of premalignant or malignant cell or larger than the approximate size of a premalignant or malignant cell to produce a fourth representation, and eliminating the images in the fourth representation from the images in the third representation to produce a representation having substantially only images the approximate size of a premalignant or malignant cell.

OTHER PUBLICATIONS

Vrolijk et al., "LEYTAS: A System for the Processing of Microscopic Images", *Analytical and Quantitative Cytology*, vol. 2, No. 1, pp. 41-48 (The International Academy of Cytology Mar.-Apr., 1980).

Lloyd et al., "Multiprocessing Interval Processor for Automated Cytogenetics", *Applied Optics*, vol. 26, No. 16, pp. 3356 (Optical Society of America Aug. 15, 1987).

Pycock et al., "Use of the MAGISCAN Image Analyser in Automated Uterine Cancer Cytology", *Analytical and Quantitative Cytology*, vol. 2, No. 3, pp. 195-202 (The International Academy of Cytology Sep. 1980).

Tucker, "Automated Screening of Cervical Smears", *Machine Perception of Patterns and Pictures*, pp. 88-96, (Proceedings of the Conference Organized by the Physics in Industry Subcommittee of the Institute of Physics in collaboration with The National Physical Laboratory and The Institution of Electrical Engineers held at The National Physical Laboratory, Teddington, Middlesex, Massachusetts, 12-14 Apr. 1972).

Tanaka et al., "Fundamental Study on An Automatic Cytoscreening System Utilizing The Pattern Recognition System, III, A New System of Automated Apparatus (CYBEST) Utilizing The Pattern Recognition Method", *Proceedings of the International Conference of Automation of Uterine Cancer Cytology*, (Tutorials of Cytology 1976).

Kasdan et al., "High Performance Pathology Workstation using an Automated Multispectral Microscope", *Applied Optics*, vol. 26, No. 16, pp. 3294-3300, (Optical Society of America Aug. 15, 1987).

Green entitled "A Practical Application of Computer Pattern Recognition Researcch: The Abbott ADC-500 Differential Classifier", *The Journal of Histochemistry and Cytochemistry*, vol. 27, No. 1, pp. 160-173 (The Histochemistry Society, Inc. 1979).

Green entitled "Parallel Processing in a Pattern Recognition Based Image Processing System: The Abbott ADC-500™ Differential Counter", *IEEE Computer Society Conference on Pattern Recognition and Image Processing*, pp. 492-498 (IEEE ©1978).

Publication entitled "The Second International Conference on Artificial Intelligence Systems (EXPERT SYSTEMS) as Diagnostic Consultants for the Cytologic and Histologic Diagnosis of Cancer", *Abstracts*, (The International Academy of Cytology, American Society of Cytology, The Tutorials of Cytology at the University of Chicago, Mar. 13-15, 1988) (Held at the Drake Hotel Chicago IL).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicated additions made to the patent.

AS A RESULT OF REEXAMINATION, IT HAS BEEN DETERMINED THAT:

The patentability of claims 11–20 is confirmed.

Claims 1 and 21 are determined to be patentable as amended.

Claims 2–10, dependent on an amended claim, are determined to be patentable.

1. A method of classifying objects in a *fixed* cytological specimen, comprising the steps of:
 a) obtaining a first image of at least part of such cytological specimen;
 b) classifying objects in such first image on the basis of a predetermined criteria;
 c) selecting at least one object for display based on said classifying;
 d) obtaining a second image of at least part of such cytological specimen containing said at least one selected object; and
 e) displaying at least part of such second image to produce a visual display of said at least one selected object.

21. An apparatus for classifying objects in a *fixed* cytological specimen, comprising:
 means for obtaining a first image of at least part of such cytological specimen;
 means for classifying objects in such first image on the basis of a predetermined criteria;
 means for selecting at least one object for display based on classification performed by said means for classifying;
 means for obtaining a second image of such cytological specimen containing said at least one selected object; and
 means for displaying at least part of such second image to produce a visual display of said at least one object.

* * * * *